US007514851B2

(12) United States Patent
Wilser et al.

(10) Patent No.: US 7,514,851 B2
(45) Date of Patent: Apr. 7, 2009

(54) CURVED CAPACITIVE MEMBRANE ULTRASOUND TRANSDUCER ARRAY

(75) Inventors: Walter T. Wilser, Cupertino, CA (US); Sean T. Hansen, Palo Alto, CA (US); Grazyna M. Palczewska, Bellevue, WA (US); Stephen R. Barnes, Bellevue, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 457 days.

(21) Appl. No.: 11/181,520

(22) Filed: Jul. 13, 2005

(65) Prior Publication Data

US 2007/0013264 A1 Jan. 18, 2007

(51) Int. Cl.
*H04R 17/00* (2006.01)
*H01L 41/08* (2006.01)
*A61B 8/00* (2006.01)

(52) U.S. Cl. ...................................... 310/334; 600/459

(58) Field of Classification Search ................. 310/334; 600/459

See application file for complete search history.

(56) References Cited

U.S. PATENT DOCUMENTS

| | | | | |
|---|---|---|---|---|
| 5,671,746 | A | 9/1997 | Dreschel et al. | |
| 2004/0000847 | A1 | 1/2004 | Ladabaum et al. | |
| 2004/0190377 | A1 | 9/2004 | Lewandowski et al. | |
| 2005/0146247 | A1 * | 7/2005 | Fisher et al. | 310/334 |
| 2006/0241473 | A1 * | 10/2006 | Kuniyasu | 600/459 |

FOREIGN PATENT DOCUMENTS

| | | | |
|---|---|---|---|
| EP | 458092 | A2 * | 11/1991 |
| JP | 61256900 | A * | 11/1986 |
| JP | 07327299 | A * | 12/1995 |
| JP | 08089505 | A * | 4/1996 |

* cited by examiner

*Primary Examiner*—Jaydi SanMartin

(57) ABSTRACT

CMUT elements are formed on a substrate. Electrical conductors are formed to interconnect between different portions of the substrate. The substrate is then separated into pieces while maintaining the electrical connections across the separation. Since the conductors are flexible, the separated substrate slabs may be positioned on a curved surface while maintaining the electrical interconnection between the slabs. Large curvatures may be provided, such as associated with forming a multidimensional transducer array for use in a catheter. The electrical interconnections between the different slabs and elements may allow for a walking aperture arrangement for three dimensional imaging.

12 Claims, 1 Drawing Sheet

CURVED CAPACITIVE MEMBRANE ULTRASOUND TRANSDUCER ARRAY

BACKGROUND

The present invention relates to curved ultrasound transducer arrays. In particular, a curved capacitive membrane ultrasound transducer (CMUT) type of array is provided.

A curved one dimensional array of piezoelectric type elements allows scanning in sector formats. The elements of the array are separated by dicing. The resulting kerfs are filled with an epoxy or other flexible material or left empty. The flexible array of elements is bent or curved. The kerf filling material, such as epoxy, provides the flexibility for positioning the array without damage. However, piezoelectric ceramics may be expensive or difficult to manufacture and may have some undesired acoustical properties.

Another type of transducer includes one or more microelectromechnical devices (e.g., a CMUT). A flexible membrane positioned over a cavity or chamber transduces between acoustical energies through flexing of the membrane and electrical energies by variation in potential between electrodes adjacent the membrane. By providing an electrode in a chamber, variance in distance between the electrodes has a capacitive effect. The CMUT elements of one or more membranes are formed on semiconductor materials using semiconductor processes. A flat transducer array is manufactured on a silicon wafer. However, silicon wafers are generally not flexible.

Semiconductor material may be thinned or made thin enough to allow flexing of the array for a curved CMUT. However, the amount of flexing of the substrate is limited. Thinning the substrate may result in a more fragile wafer which is more likely to get damaged during manufacturing and use.

BRIEF SUMMARY

By way of introduction, the preferred embodiments described below include curved capacitive membrane ultrasound transducers, curved multidimensional transducer arrays, methods for manufacturing a curved capacitive membrane transducer and methods for three dimensional imaging. CMUT elements are formed on a substrate. Electrical conductors are formed to interconnect between different portions of the substrate. The substrate is then separated into pieces while maintaining the electrical connections across the separation. Since the conductors are flexible, the separated substrate slabs may be positioned on a curved surface while maintaining the electrical interconnection between the slabs. Large curvatures may be provided, such as associated with forming a multidimensional transducer array for use in a catheter. The electrical interconnections between the different slabs and elements may allow for a walking aperture arrangement for three dimensional imaging. Any one or more of the features described above may be used alone or together.

In a first aspect, a curved capacitive membrane ultrasound transducer is provided. A plurality of substrates is arranged along a substantially curved surface. Each substrate has at least one capacitive membrane transducer cell. An electrical interconnection is provided between the substrates.

In a second aspect, a method is provided for manufacturing a curved capacitive membrane ultrasound transducer. One or more conductors are formed, which interconnect different portions of a substrate. The substrate is separated between first and second elements of one or more membranes. The conductor interconnects across the separated substrate and is maintained after separation of the substrate.

In a third aspect, an ultrasound transducer is provided for a curved, multidimensional array. A plurality of slabs of semiconductor material is provided. The slabs are each separated at least in part from other slabs by a notch. The slabs are arranged along a curved surface. At least one transducer cell is in or on each of the slabs. At least one connector or conductor extends between the slabs.

In a fourth aspect, a method is provided for three dimensional imaging. Different rows of elements of a multidimensional capacitive membrane ultrasound transducer array are sequentially selected. The rows are on different slabs positioned along a curved surface. For each row selection, signals are used along different columns of the elements. The elements of each column electrically interconnect across the slabs.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

To form a curved array from a CMUT or semiconductor wafer, the array is cut, etched, or broken into strips. The strips may then be arranged in a curved pattern. To maintain electrical connection between the strips despite the cutting, metal bridges or conductors are maintained in connection between the various strips. Alternatively, additional connections are formed after cutting, such as using flex circuits or tabs of conductive materials. By having conductors between the strips, the strips may be bent relative to each other to allow the array to form a curved shape without destroying the conductive metal bridges.

Figure 1:
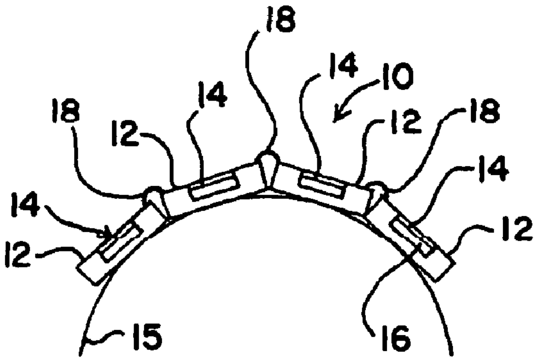
FIG. 1 is a cross-sectional diagram of one embodiment of a curved CMUT.
Figure 2:
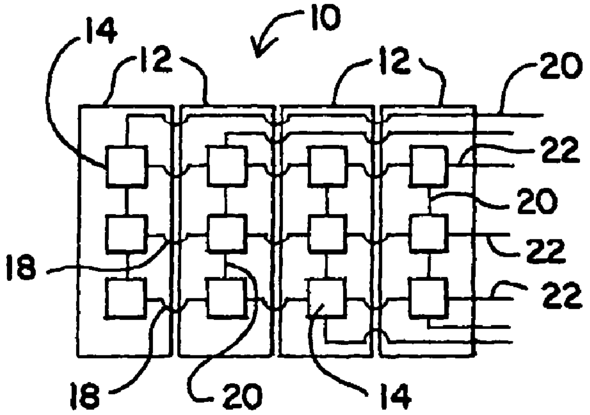
FIG. 2 is a top view of a curved CMUT in a multidimensional array.

FIGS. 1 and 2 show an ultrasound transducer 10. The transducer 10 is a curved CMUT. In the example shown in FIG. 2, the curved transducer 10 is a curved multidimensional array. The transducer 10 includes a plurality of slabs of substrates 12, ultrasound transducer elements 14, electrical interconnections 18, and conductors 20 and 22. Additional, different or fewer components may be provided. For example, additional substrates 12 are provided, such as for use in a 64, 96, 128 or other number of element one dimensional array. Additional elements 14 may be provided in a one or two dimensional array. As another example, different conductor 20, 22 and/or electrical interconnections 18 may be used.

The substrates 12 are slabs of semiconductor or other material that can be processed to form the transducer elements and electrical interconnections. For example, the substrates 12 are formed from a silicon wafer. Other semiconductor materials may be used. Slab is used as a general term for a plate, strip, block, beam, or other shape.

A plurality of slabs of substrates 12 is provided. The substrates 12 are formed from a same wafer, so have similar structures. Alternatively, different wafers are used for different substrates 12. The substrates 12 are positioned adjacent to each other, such as each substrate 12 being within at least one substrate width of another one of the substrates 12. The substrates 12 are in contact with additional substrates or closely abutted. Epoxy, kerf filling material, bonding, pressure, or other force or material maintains the substrates 12 in the desired relative position.

Figure 3:
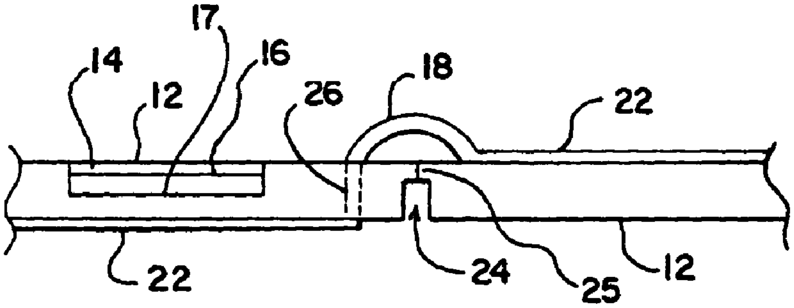
FIG. 3 is a cross-sectional diagram showing a portion of a CMUT to be used on a curved array.

Referring to FIG. 3, each of the substrates 12 is separated by an adjacent substrate by a notch 24. As shown in FIG. 3, the notch 24 extends only part way through a thickness of the substrates 12. A substrate bridge joins the two substrates 12. The bridge is thinner than either of the joined substrates 12. When positioned on a curved surface as shown in FIG. 1, the substrate bridge is more flexible, allowing bending. Alternatively, the bridge cracks, separating, at least partially or entirely, the two substrates 12. FIG. 3 shows a crack 25 at or between the two substrates 12 and across the bridge. The crack 25 in the common substrate completely or partially separates the two slabs of substrate 12. The crack 25 is formed prior to or after bending of the substrates 12 relative to each other. By separating adjacent substrates 12 by the notch 24 and/or the crack 25, one substrate 12 may be rotated with respect to the other substrate 12 for forming a curved array. Even when completely separated, the notch 24 separates at least partially one slab of substrate 12 from another slab of substrate 12.

The notch 24, the crack 25 or the thin bridge of substrate material allow the slabs of substrate 12 to be positioned along a curved surface 15 as shown in FIG. 1. The substrates 12 are arranged along the curved surface 15. The curved surface has any desired shape, such as a cylindrical, spherical, or ellipsoid surface. While a constant radius of curvature is shown in FIG. 1, curves with varying radii, concave, convex, spherical, or other complex curvature as well as flat structures may be used. The transducer 10 and corresponding substrates 12 approximate the curvature of the surface. For example, the substrates 12 are generally flat. By aligning a plurality of adjacent substrates 12 at different angles relative to each other, a generally or substantially curved array is provided.

Each substrate 12 includes one or more transducer elements 14. In one embodiment, each transducer element 14 is a capacitive membrane transducer type of element. One or more flexible membranes 16 are provided over respective chambers or gaps 17 as shown in FIGS. 1 and 3. While shown as a single membrane 16 and gap 17 for ease of reference, each element 14 may include a plurality of such structures electrically interconnected as a single element 14. An electrode positioned on the membrane 16 and another electrode positioned within the chamber or gap 17 in conjunction with the flexibility of the membrane 16 acts to transduce between electrical and acoustical energies. The transducer element 14 is formed using either CMUT or other micro-electro mechanical manufacturing techniques, such as semiconductor manufacturing techniques. Other substrate based, micro-electro mechanical, or capacitive based transducer elements may be used. For example, a beam rather than a membrane is provided. A hole, gap or other structures may be provided through the membrane 16, such as a hole used for etching away insulator material to form the chamber 17.

Each slab of substrate 12 includes at least one transducer element 14. A given transducer element 14 may include a single or a plurality of cells, such as the membranes 16 and associated structures. As shown in FIG. 1, each slab of substrate 12 includes a single element 14. Alternatively, each slab 12 includes a plurality of elements extending along an azimuth and/or elevation direction.

FIG. 2 shows use in a multidimensional array. Each slab of substrate 12 includes at least three elements 14. While shown as only three elements long, the columns may have any number of elements 14. In one embodiment, 16, 32, 64, 96 or other number of elements 14 are provided in each of the columns. At least one column of elements 14 is provided for each of the slabs of substrates 12. In alternative embodiments, a plurality of columns of elements 14 is provided on each of the substrates 12. For the multidimensional array 10, the elements 14 also have rows of elements 14. A row of elements 14 extends across a plurality of different substrates 12. Any number of rows may be provided. The columns and the rows of elements 14 provide for a multidimensional array 10, such as a N by M array of elements where M and N are both greater than 1. Hexagonal, triangular or other element distribution patterns may alternatively be used.

FIG. 2 shows substrates 12 and associated elements 14 for arrangement along a cylindrical surface. For a spherical or other more complex curvature, the substrate 12 may be separated along the column extent as well as the row extent of elements 14.

In one embodiment represented by FIG. 1, the transducer 10 is positioned on a cylindrical surface for providing a multidimensional array. The cylindrical surface corresponds to a catheter. For example, a 20 by 20 element multidimensional array is provided for use within a catheter having a radius of curvature of about 3 millimeters or less. 20 columns of elements are on 20 or fewer substrates 12. An acoustically transparent material surrounds the transducer 10 within the catheter. Alternatively, the transducer 10 is positioned on the catheter. Uses in handheld, transesophageal, endocavity, or intravascular probes are alternatively provided.

The electrical interconnects 18 are conductors, such as a gold, copper, silver, other metal or other now known or later developed conductor that is flexible enough to withstand the degree of curvature. Each interconnector 18 is a few microns thick, but greater or less thicknesses may be provided depending on the degree of flexibility required for the curvature. In one embodiment, the interconnector 18 is a metallized conductor extending between the substrates 12. As shown in FIG. 3, the interconnect 18 is formed while the substrates 12 are connected together or are a common substrate. Using lithography, metallization, patterning, etching, depositing, sputtering or other semiconductor process, the interconnector 18 extending between sections of a common substrate that will become two different substrates 12 is formed.

In one embodiment shown in FIG. 3, the interconnect 18 is a bridge structure with an air gap underneath. For example, gold is deposited over an insulator by sputtering. The sputtered gold is patterned. The insulator is etched away leaving an air gap and forming a conductive bridge. In an alternative embodiment, the interconnection 18 is formed flat on the common substrate. Electroplating or evaporation can also be used to deposit the metal bridges.

As shown in FIGS. 2 and 3, the interconnects 18 connects with different conductors 20 and 22. The conductors 20 and 22 are on a same or opposite side as the interconnect 18. For example, FIG. 3 shows a via 26 connecting the interconnect 18 through the substrate 12 to the conductor 22. The different conductors 20 and 22 are signal traces, vias, doped-silicone, or other conductors connected with the element 14. The interconnects 18 are formed at a same time, with a same process or differently than the conductors 20, 22. For example, the interconnections 18 are a signal trace deposited or patterned to form the conductors 20, 22 without additional processing.

One type of conductor 22 provides signals to signal electrodes of the elements 14. Another type of conductor 20 provides bias voltages to the element 14. Yet another conductor provides grounding connections to the elements 14. Additional or different electrical connections to the elements 14 may be provided. For use as a completely independently activated array of elements, a different signal conductor 20 is provided for each element 14. For use in a walking aperture, the same signal conductor 22 may connect with all or some of the elements 14 in a row of elements as shown in FIG. 2. The same biased voltage conductor 20 connects with all the elements 14 or a subset elements 14. For example and as use in a walking aperture, different bias voltage conductors 20 are provided for different columns of elements 14. Bias voltage conductors 20 can be used for selectively activating the different rows. Other arrangements of electrical connection to, between, within and/or through the elements 14 using the interconnections 18 may be provided.

In another embodiment, one or more of the substrates 12 include electronics, such as amplifiers, multiplexers or switches. The electronics are provided on the same substrates 12 as the elements 14. Alternatively, one or more of the substrates 12, such as substrates 12 on the ends of the array or spaced within the array, include the electronics without any elements 14. The substrates 12 with the electronics electrically connect with one or more other substrates across a separation for forming a curved array with reduced area. The electronics are then provided as part of the array, such as in a catheter.

Figure 4:
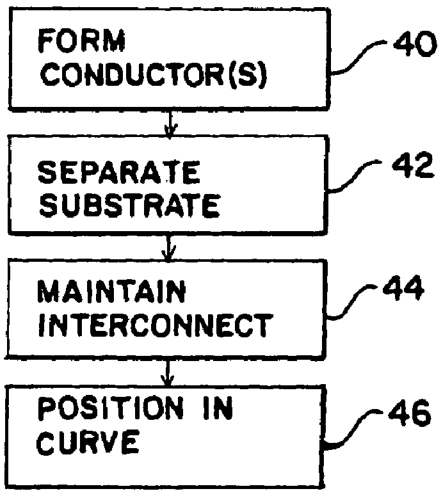
FIG. 4 is a flowchart diagram of one embodiment of a method for manufacturing a curved multidimensional transducer array.

FIG. 4 shows one embodiment of a method for manufacturing a curved capacitive membrane ultrasound transducer or other substrate based transducer. The method results in the transducers described above in FIGS. 1, 2 or 3 or other transducers. Additional, different or fewer acts than showed in FIG. 4 may be provided. For example, the process may be provided without the positioning of act 46. The acts may be performed in a different order than shown in FIG. 4, such as separating the substrate in act 42 prior to forming the conductors in act 40.

In act 40, a conductor is formed. The conductor connects with one or more elements of a substrate, such as forming signal traces associated with a same type of electrode (e.g., signal, grounding or bias) of a capacitive membrane type of element. The conductor is formed by photolithography, other type of lithography, metallizing, patterning, depositing, etching or combinations thereof. For example, the conductor is formed on one surface of a common substrate at a same or different time as forming signal traces or electrodes for elements. Using patterning, etching, sputtering, deposition or other technique, a metallic conductor is deposited directly on semiconductor substrate or on top of layers of other material on the substrate. The formation of the conductor provides the desired interconnections, such as between elements to between an element and a cable.

The conductor is formed over a portion of a common substrate. For example, the conductor is formed between two signal traces, vias, electrodes, or other conductive structures. Alternatively, the conductor is formed as a trace, electrode or other electrode structure. A single conductor or a plurality of conductors is formed. Each conductor is electrically isolated from the other conductors or has a common electrical connection with another conductor.

The conductors are all formed along one or more ridge lines, linear positions, or other positions associated with eventual separation. The conductors bridge the separation locations. In one embodiment, the conductors are provided in column and row patterns for signal and bias conductors as shown and described with respect to FIG. 2. The conductors are provided as part of the signal or bias traces with the same or different metal or structure.

In act 42, a common substrate is separated. Separation is provided between different elements, such as between different capacitive membrane elements. For example, separation is provided between rows of elements. Separation is between every row, every other or other constant or variable frequency number of elements or rows of elements. The conductors connect across the separations. Alternatively, the separation is between different cells of a same element.

The separation of the substrate is provided by forming a notch. The notch is formed at least partially through the common substrate. For example, the notch only extends a portion of the way through the substrate. A bridge extending between two substrate structures is then provided. The bridge may remain but is thin enough to provide some flexibility. The notch with the flexible bridge still provides separation between two substrates, but separation with both a substrate bridge and for the conductors still interconnecting the substrate structures. Alternatively, the substrate is then broken at the notch, separating the bridge through a fracture. In yet another alternative embodiment, the notch extends all the way through the substrate. Complete separation is provided by bending the common substrate, causing a crack or breakage over the bridge formed by the notch. The fracture allows formation of a bending or bendable section. The notch does not extend through the conductor.

The notch is formed using a dicing saw, etching, scoring, or other technique. For example, a plasma etch is provided to etch through the substrate material but not through a metallic conductor.

In act 44, the conductor interconnecting the different substrates and associated elements is maintained after separating the common substrate. The conductor is maintained by preventing a notch from extending through the conductor. Since the conductor is at least partially flexible, the bending and separation of the substrate is provided while still also maintaining the electrical interconnection. For example, the bending or separation of the different substrates is provided at part of the stacking and bonding of the transducer. The common substrate with notches or other separation is placed on a curved surface and bound to the curved surface. The placing causes the separation, such as a fragment where complete separation between adjacent substrates is provided. Since the bonding maintains the substrate in position, additional forces further separating the substrates may be avoided. As a result, the flexible conductor interconnecting the two substrates is maintained, even if pulled, stretched or twisted.

In act 46, the common substrate with notches distinguishing separate substrates or a plurality of completely separated separate substrates are positioned along a curved surface. As discussed above, the positioning along the curved surface may cause the further, initial, complete and/or partial separation through cracking. The notch or other separation allows for positioning of the semiconductor material substrates along the curved surface without undesirably damaging the transducer array.

The curved transducer is used for ultrasound imaging, such as transducing between electrical and acoustical energies. In one embodiment, the one dimensional or two dimensional array with separately addressable elements is provided for electronic steering in any desired or possible direction. In an alternative embodiment, a multidimensional transducer array is provided for three dimensional imaging with a walking aperture. Different rows or columns of elements are sequentially selected. At least two of the rows or columns are on different slabs of substrate positioned along a curved surface. The columns are selected by providing a bias voltage for efficient operation of a membrane of a capacitive membrane ultrasound elements. Columns that are not selected at a given time have a different bias or no bias applied. Different columns are selected at different times for walking a single columns or multi column transmit aperture across the face of the array. Since the array is on a curved surface, different transmit aperture columns correspond to scanning different scan planes within a volume.

For each column selection, transmit signals are provided along rows of elements. The signals are relatively delayed and apodized for azimuthal steering along the row direction. Along a given row, inactive and active elements connect with a same signal trace. The active or selected elements generate acoustic energy or received electrical signals, and the inactive elements contribute little or no signal information or acoustic generation. The interconnections across slabs of substrate allow for application of the different bias as well as signals to or from the various elements.

Use of a walking aperture may reduce the total number of cables or other conductors for interconnecting a transducer with an imaging system. For use in a catheter for three or four dimensional imaging, a walking curved aperture minimizes the number of conductors routed through the catheter. CMUT arrays or other micro-electro mechanical structures may be used for the transducer within a catheter.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A curved capacitive membrane ultrasound transducer comprising:

a plurality of substrates arranged along a substantially curved surface, each substrate having at least one capacitive membrane transducer cell; and an electrical interconnection between the substrates of the plurality, wherein the electrical interconnection, between the substrates, is separate from the substrates.

2. The transducer of claim 1 wherein the plurality of substrates comprise a plurality of plates of semiconductor material, each plate having at least one capacitive membrane transducer cell.

3. The transducer of claim 1 wherein the curved surface comprises a cylindrical, spherical, or ellipsoid surface.

4. The transducer of claim 3 comprising a multi-dimensional array of the capacitive membrane transducer elements on or in a catheter.

5. The transducer of claim 1 wherein the plurality of substrates are adjacent each other, each substrate within at least one substrate width of another one of the substrates.

6. The transducer of claim 5 wherein the adjacent substrates are joined by a substrate bridge, the substrate bridge being thinner than the joined substrates.

7. The transducer of claim 5 wherein the adjacent substrates are separated by a crack formed in a common structure.

8. The transducer of claim 1 wherein the electrical interconnection comprises a conductive bridge.

9. The transducer of claim 1 wherein the electrical interconnection comprises a metallized conductor extending between adjacent substrates.

10. The transducer of claim 1 wherein the at least one capacitive membrane transducer cell is part of first element, the first element having a plurality of capacitive membrane transducer cells, the first element being one in a first row of a plurality of rows of elements, each element having one or more of the capacitive membrane transducer cells, and wherein the electrical interconnection comprises separate conductors connecting across the plurality of substrates with columns of elements and bias conductors for selectively activating different ones of the rows of elements.

11. The transducer of claim 1 wherein at least one of the substrates includes electronics.

12. A curved capacitive membrane ultrasound transducer comprising:

a plurality of substrates arranged along a substantially curved surface, each substrate having at least one capacitive membrane transducer cell and each substrate being completely separated from each other; and an electrical interconnection bridging between the completely separated substrates of the plurality.

* * * * *